US010234461B2

(12) United States Patent
Stevenazzi et al.

(10) Patent No.: US 10,234,461 B2
(45) Date of Patent: Mar. 19, 2019

(54) ANALYSIS OF THE MOLECULAR WEIGHT DISTRIBUTION OF COMPLEX POLYPEPTIDE MIXTURES

(71) Applicant: Chemi S.P.A., Cinisello Balsamo (IT)

(72) Inventors: Andrea Stevenazzi, Cinisello Balsamo (IT); Andrea Distaso, Cinisello Balsamo (IT); Aureliano Gaiassi, Cinisello Balsamo (IT); Eleonora Spuria, Cinisello Balsamo (IT); Silvana Cappelletti, Cinisello Balsamo (IT)

(73) Assignee: CHEMI S.P.A., Cinisello Balsamo (MI) (IT)

( * ) Notice: Subject to any disclaimer, the term of this patent is extended or adjusted under 35 U.S.C. 154(b) by 132 days.

(21) Appl. No.: 15/273,718

(22) Filed: Sep. 23, 2016

(65) Prior Publication Data
US 2017/0089916 A1 Mar. 30, 2017

(30) Foreign Application Priority Data
Sep. 24, 2015 (EP) ..................................... 15186742

(51) Int. Cl.
*G01N 33/00* (2006.01)
*G01N 33/68* (2006.01)

(52) U.S. Cl.
CPC ..... *G01N 33/6848* (2013.01); *G01N 33/6803* (2013.01)

(58) Field of Classification Search
CPC ....................... G01N 33/6848; G01N 33/6803
See application file for complete search history.

(56) References Cited

U.S. PATENT DOCUMENTS

| | | | |
|---|---|---|---|
| 3,849,550 A | 11/1974 | Arnon et al. |
| 5,800,808 A | 9/1998 | Konfino et al. |
| 6,514,938 B1 | 2/2003 | Gad et al. |
| 6,800,287 B2 | 10/2004 | Gad et al. |
| 7,074,580 B2 | 7/2006 | Gad et al. |
| 7,163,802 B2 | 1/2007 | Gad et al. |
| 7,615,359 B2 | 11/2009 | Gad et al. |
| 8,399,211 B2 | 3/2013 | Gad et al. |
| 2002/0115103 A1 | 8/2002 | Gad et al. |
| 2007/0059798 A1 | 3/2007 | Gad et al. |
| 2013/0205877 A1* | 8/2013 | Srinivasan ............ B01D 15/34 73/61.52 |
| 2014/0045740 A1 | 2/2014 | Glajch et al. |

FOREIGN PATENT DOCUMENTS

| | | |
|---|---|---|
| WO | 0018794 A | 4/2000 |
| WO | 2012016042 A3 | 5/2012 |
| WO | 2012123959 A2 | 9/2012 |

OTHER PUBLICATIONS

Agilent Technologies. "Polymer molecular weight distribution and definitions of MW averages." Technical Overview published Apr. 2015. (Year: 2015).*
Espinosa-De-La-Garza, C. et al., "Analysis of therapeutic proteins and peptides using multi angle light scattering coupled to ultra high performance liquid chromatography", Journal of Separation Science, vol. 3, Issue 9, May 2015 pp. 1537-1543.
Mori S., et al., "Size Exclusion Chromatography," Springer 1999, pp. 101-104.
Oliva A., et al., "Comparative study of protein molecular weights by size-exclusion chromatography and laser-light scattering," Journal of Pharmaceutical and Biomedical Analysis 25(2001) 833-841.
Ramot Y., et al., "Comparative long-term preclinical safety evaluation of two glatiramoid compounds (glatiramer acetate, copaxone, and TV-5010, Programer) in rats and monkey," Toxicologic Pathology, 40: 40-54, 2012.
Search Report and Written Opinion of EP15186742.1 dated Feb. 17, 2016.
Teitelbaum D, et al., "Suppression of Experimental Allergic Encephalomyelitis by a Synthetic Polypeptide," Eur. J. Immunol. 1971 1:241-248.

* cited by examiner

*Primary Examiner* — Christopher Adam Hixson
(74) *Attorney, Agent, or Firm* — Silvia Salvadori, P.C.; Silvia Salvadori

(57) ABSTRACT

The present invention relates to simple size exclusion chromatography (SEC) analytical methods useful for the assessment of accurate molecular weight distributions (MWDs) of certain polypeptide mixtures known as glatiramoids. The use of a SEC method based on one or more broad MWD standards furnishes the absolute (not relative) molecular weight distribution profile of complex polypeptide mixtures like, for instance, the glatiramer acetate (GA) polymer.

16 Claims, 7 Drawing Sheets

ANALYSIS OF THE MOLECULAR WEIGHT DISTRIBUTION OF COMPLEX POLYPEPTIDE MIXTURES

This utility application claims priority to and the benefit of European patent application No. 15186742.1 filed on Sep. 24, 2015, the content of which is incorporated herein by reference in its entirety.

The present invention relates to simple size exclusion chromatography (SEC) analytical methods useful for the assessment of accurate molecular weight distributions (MWDs) of certain polypeptide mixtures known as glatiramoids. The use of a SEC method based on one or more broad MWD standards furnishes the absolute (not relative) molecular weight distribution profile of complex polypeptide mixtures like, for instance, the glatiramer acetate (GA) polymer.

BACKGROUND OF THE INVENTION

Glatiramoids are a family of synthetic copolymers containing four amino acids: L-glutamic acid, L-alanine, L-lysine and L-tyrosine, in a defined molar ratio (Varkony et al. 2009). Glatiramer acetate (GA) is a member of the glatiramoid family, and it is the active pharmaceutical ingredient of the commercially available medicine Copaxone® (Teva Pharmaceutical Industries Ltd., Israel), indicated for the treatment of patients with relapsing forms of multiple sclerosis.

According to the product labeling, GA consists of the acetate salts of synthetic polypeptides, containing four naturally occurring amino acids: L-glutamic acid, L-alanine, L-tyrosine, and L-lysine with an average molar fraction of 0.141, 0.427, 0.095, and 0.338, respectively. The average molecular weight of GA ranges from 5,000 to 9,000 daltons.

Chemically, GA is designated L-glutamic acid polymer with L-alanine, L-lysine and L-tyrosine, acetate (salt). Its structural formula is:

(Glu,Ala,Lys,Tyr)$_x$·xCH$_3$COOH

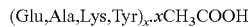

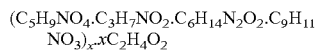

CAS—147245-92-9

(NDA 020622/S-089 FDA Approved Labeling Text dated Jan. 28, 2014)

GA is synthesised via amino acid polymerisation followed by a subsequent cleavage or partial depolymerisation step. Because of the stochastic nature of polymerisation and cleavage reactions, the polypeptides obtained by this process vary in sequence, length and molecular weight (MW), resulting in a characteristic molecular weight distribution (MWD) that spans from about 2,500 to 20,000 daltons.

The average MW and the MWD represent important characteristics to distinguish GA from other glatiramoids or similar polypeptide mixtures. In fact, differences in the MWD profile may be both indicative of a different manufacturing process and partially predictive of a different biological activity. When compared to GA, high MW copolymers are highly immunogenic and toxic, whereas low MW glatiramoids show lower biological potency in pharmacological models (Ramot et al. 2012).

The MWD, or molar mass distribution, of a polymer describes the relationship between the number of moles of each polymer species ($N_i$) and the molar mass ($M_i$) of that species. The MWD may be represented either graphically, i.e. as a cumulative or differential curve (see FIGS. 5 and 6), or in a numeric way, as a table where the cumulative MWD is represented reporting the mass percentage of the macromolecules having molecular weight smaller than or equal to a specified value (see Table 1).

Alternatively, the MWD may be represented by calculating the most common molecular weight averages. Different average values, or moments, can be defined, depending on the statistical formula that is applied. In practice, at least three averages are used:

Number average molar mass: $M_n = \Sigma(N_i M_i)/\Sigma M_i$

Weight average molar mass: $M_w = \Sigma(N_i M_i^2)/\Sigma(N_i M_i)$

Z-average molar mass: $M_z = \Sigma(N_i M_i^3)/\Sigma(N_i M_i^2)$

Dispersity: $D = M_w/M_n$

Where $N_i$ is the number of molecules with molar mass $M_i$.

If the polymer is a homogeneous ("monodisperse") sample, then all the molecular weight averages are equivalent. In the case of a heterogeneous ("polydisperse") polymer sample, the ratio of $M_w$ to $M_n$ ($D = M_w/M_n$) and that of $M_z$ to $M_w$ ($M_z/M_w$) are measures of the dispersity (heterogeneity) of the MWD.

Size exclusion chromatography (SEC) is a chromatographic technique that separates molecules in solution by their molecular size, or more precisely, by their hydrodynamic volume. The SEC stationary phase is a porous material with a characteristic pore size distribution, and depending on molecular size, a larger or lesser fraction of the pores is accessible to the macromolecules. Accordingly, the elution volume of a solute increases as its molecular size decreases. When properly calibrated, a SEC system is the most convenient method for the determination of the overall MWD of a polymer such as GA.

Two different strategies or methods are described in patent literature for obtaining the molecular weight distribution of a polypeptide mixture via SEC. The first group of methods provides values of molecular weight based on a calibration obtained with a set of monodisperse standards. These standards are either single molecules (obtained by synthesis or recombinant DNA technology) or mixtures with narrow MWD obtained by fractionation of a glatiramoid sample and in all cases are different from real GA.

A second group of methods provides "absolute" values of the molecular weight generally using a molecular weight sensitive detector, e.g. a Right-Angle Light Scattering (RALS), a Low-Angle Light Scattering (LALS), RALS/LALS hybrids or a Multi-Angle Light Scattering (MALS), usually combined with a concentration detector, either based on refractive index (RI) or ultraviolet absorption (UV).

There are numerous patents (U.S. Pat. No. 6,514,938, U.S. Pat. No. 6,800,287, U.S. Pat. No. 7,074,580, U.S. Pat. No. 7,163,802, U.S. Pat. No. 7,615,359 and U.S. Pat. No. 8,399,211) teaching how to use standards made of single polypeptide molecules for the calibration of SEC columns employed in the determination of MWD of batches of GA. The need of using a set of dedicated standards depends on the particular structural characteristics of GA polypeptides. SEC fractionation is regulated by molecular hydrodynamic volume, so the MWD of a copolymer can be accurately estimated only if the MW standards have the same higher order structure—and thus, the same density or partial specific volume—of the sample (S. Mori and H. G. Barth *Size Exclusion Chromatography*, Springer 1999, pp. 101-104). For example, using a commercial mixture of proteins as the MW standard, the obtained apparent MW of GA resulted to be higher than that one obtained using a set of GA-like peptides (see patent application US 2007/059798). This is because globular proteins are more structured than GA polypeptides, thus having a higher density (or lower partial specific volume). Accordingly, the use of "normal" commercially available protein markers is not appropriate for the determination of the MWD of GA batches.

Nonetheless, any set of polypeptide standards, either consisting of single molecules or mixtures with narrow MWD, will still be different from the GA mixture, that contains a huge number of polypeptides of different sizes that completely covers the entire range of molecular weights of the MWD. Thus, the MWD assessed by these methods can only be relative, not absolute. Moreover, it is evident that the preparation of sufficient quantities of long, pure peptides (either by chemical synthesis or by recombinant DNA technology) can be very laborious and costly.

The other approach, based on absolute SEC methods, has been recently suggested in the patent application US 2014/0045740, herein incorporated by reference: according to that teaching, every GA batch can be analysed using SEC chromatography coupled to multi-angle light scattering and refractive index detectors (SEC-MALS-RI). Although the method is "absolute" and overcomes the need for column calibration, this technique is unsuitable to be applied routinely for quality control and/or batch release purposes. Indeed, the MALS detector is subject to some practical problems: (a) a low signal to noise ratio, due to the presence of extraneous particles; (b) the high sensitivity of the MALS signal to even small and reversible aggregation phenomena. These practical problems reduce the repeatability and reproducibility of the MWD analysis by means of the SEC-MALS-RI method.

It is thus evident the need for a more practical and robust analytical method useful for determining the detailed and accurate MWD of GA and other GA-like polypeptide mixtures. Accurate evaluation of the MWD via such analytical methods is crucial for the choice of GA batches suitable for pharmaceutical use.

SUMMARY OF THE INVENTION

The present invention is based, in part, on the development of a method for assessing the molecular weight distribution (MWD) of several polypeptide mixtures. In some cases the analytical method described in the present invention may apply to copolymer mixtures containing L-glutamic acid, L-alanine, L-lysine and L-tyrosine amino acid residues in a specified molar ratio, and in some preferred cases the mixture to be analysed may be intended for the preparation of a drug product therapeutically equivalent to Copaxone®.

The method described herein entails the use of conventional size exclusion chromatography (SEC) on a suitable column set and it describes specific experimental conditions calibrated on one or more GA-like batches used as broad molecular weight standards. The broad standard calibration is a well-established technique for molecular weight determination by SEC.

In the method of the invention the broad standard is a polypeptide mixture obtained using the same procedure used for the preparation of the mixtures to be analysed; in some cases the broad standard may be a GA-like polypeptide mixture and in some preferred cases it may be a mixture showing physicochemical and biological properties similar or identical to that of Copaxone®. The broad standard(s) have substantially identical structure to the one of polypeptides batches to be analysed. Consequently, the SEC calibration and the final MWD of polypeptides can be considered as absolute.

In the method described herein the broad standard to be used as calibrant of the SEC system is preliminarily analysed using a molar mass sensitive detector such as a combination of MALS-RI or MALS-UV detectors. In such way the absolute molecular weight value of the polymer is determined at each elution volume. Using the absolute SEC-MALS-RI or SEC-MALS-UV method the experimental function Log M=f(V), where M stands for the molecular weight determined by the MALS detector and V is the elution volume, could be determined. The experimental function Log M=f(V) represents the calibration curve of the SEC system under specific conditions, which include the type of polymer and the experimental conditions. For the calibration of the SEC system, the MWD of the standard(s) can be expressed in two alternative methods: 1) by the calculated averages ($M_n$, $M_w$, $M_z$) and if known also the intrinsic viscosity; 2) by the cumulative MWD. Specifically, the cumulative MWD of the calibrant can be represented as a table reporting percentiles (e.g. 1%, 5%, . . . , 95%, 99%) and the corresponding molecular weights. Each percentile reported in the table represents the weight fraction of macromolecules in the mixture that have molecular weight smaller than or equal to the specified molecular weight value.

Using one of the two described methods (averages or cumulative MWD) commercially available SEC chromatographic software may calculate the absolute calibration curve, Log M=f(V), for any other SEC system after calibration with the same set of standards. When possible the calibration curve is linear, but also polynomial curves (typically and preferably third order) could be used.

Then, the calibration curve from the MWD standard(s) is applied to the chromatogram of polypeptides batch to be analysed (that is the signal of the concentration detector either RI or UV) to determine the whole MWD of samples, the molecular weight averages ($M_n$, $M_w$, $M_z$), the molecular weight at the peak maximum ($M_p$), molecular weight dispersity ($M_w/M_n$ and/or $M_z/M_w$).

The measured MWD, however expressed, may be compared to certain preselected value ranges, such as release specifications for active pharmaceutical ingredients (API) or for drug products, and the result, alone or together with other quality attributes, may be used to decide whether or not the examined mixture can be used for the preparation of a drug product. In some cases the MWD of GA-like polypeptide mixtures may be compared with that of a suitable number of commercial batches of Copaxone® and the result used as sameness criteria.

DEFINITIONS

Figure 1:
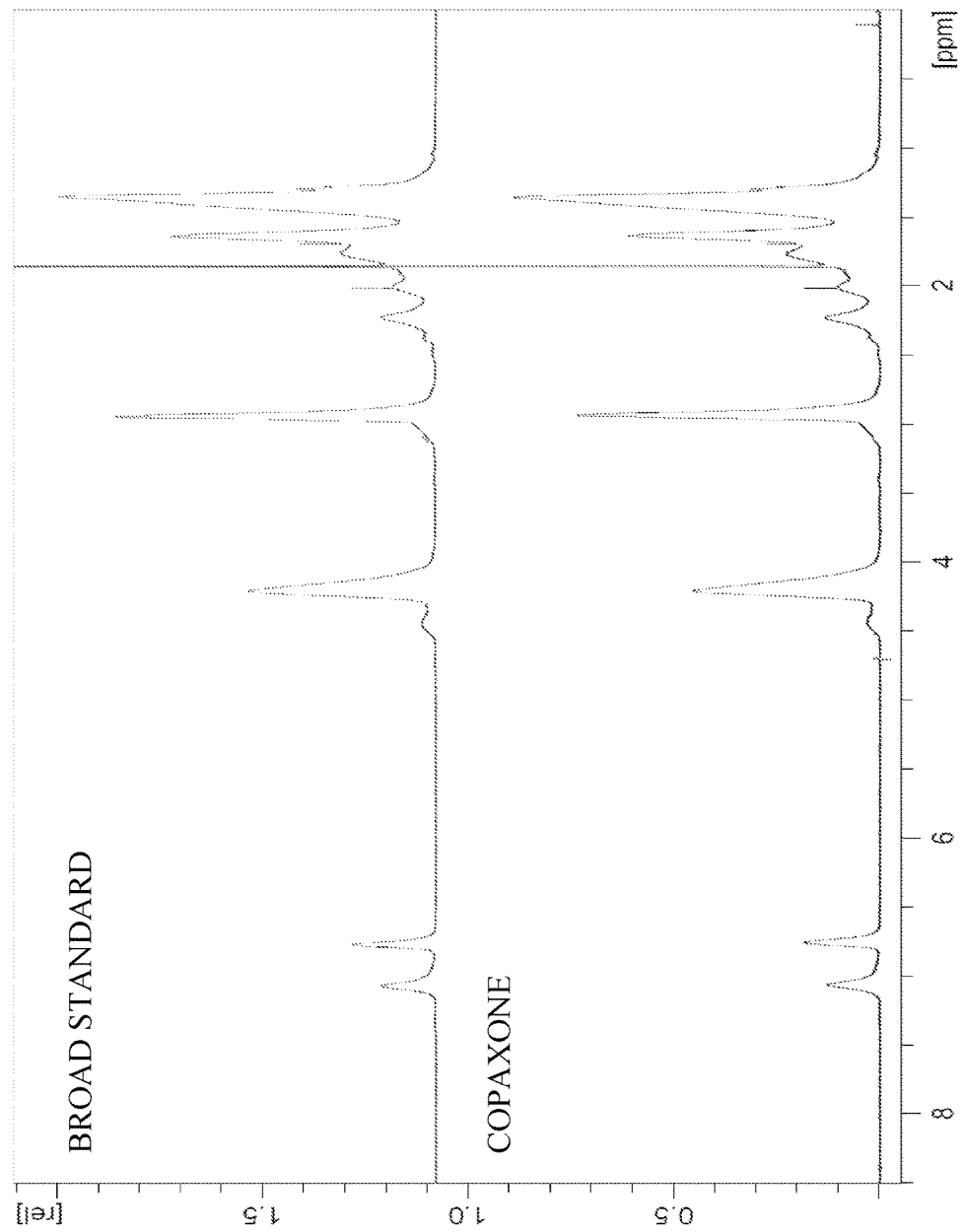
FIG. 1. NMR spectra of the broad standard (top panel) and of a batch of Copaxone® (bottom panel).

Unless otherwise defined, all terms of art, notations and other scientific terminology used herein are intended to have the meanings commonly understood by those of skill in the art to which this disclosure pertains. In some cases, terms with commonly understood meanings are defined herein for clarity and/or for ready reference; thus, the inclusion of such definitions herein should not be construed to represent a substantial difference over what is generally understood in the art.

The terms "approximately" and "about" herein refers to the range of the experimental error, which may occur in a measurement.

The terms "comprising", "having", "including" and "containing" are to be construed as open-ended terms (i.e. meaning "including, but not limited to") and are to be considered as providing support also for terms as "consist essentially of", "consisting essentially of", "consist of" or "consisting of".

The terms "consist essentially of", "consisting essentially of" are to be construed as a semi-closed terms, meaning that no other ingredients and/or steps which materially affects the basic and novel characteristics of the invention are included (optional excipients may be thus included).

The terms "consists of", "consisting of" are to be construed as a closed term.

The terms "sameness" or "sameness criteria" herein refer to those physical, chemical and/or biological drug substance(s) attributes that, according to a regulatory agency (for example, the U.S. Food and Drug Administration), should be compared to prove that a generic drug product contains the same active ingredient(s) as the innovator product. Taking Copaxone® as an example, the FDA concluded that an applicant for generic glatiramer acetate injection can demonstrate active ingredient sameness as to the following four criteria: (1) Fundamental reaction scheme; (2) Physicochemical properties including composition; (3) Structural signatures for polymerization and depolymerization; and (4) Results in a biological assay.

The term "glatiramoid" herein refers to a heterogeneous mixture of polypeptides containing four naturally occurring amino acid residues (L-glutamic acid, L-alanine, L-tyrosine, L-lysine) in a specified molar ratio, i.e. wherein the molar fraction range of L-glutamic acid is 0.129-0.153, that of L-alanine is 0.392-0.462, that of L-tyrosine is 0.086-0.100 and of L-lysine is 0.300-0.374.

The term "mixture of polypeptides" herein also includes the possible pharmaceutically acceptable salts, particularly the acetate.

The term "pharmaceutically acceptable salts" herein refers to those salts which possess the biological effectiveness and properties of the salified compound and which and which do not produce adverse reactions when administered to a mammal, preferably a human. The pharmaceutically acceptable salts may be inorganic or organic salts; examples of pharmaceutically acceptable salts include but are not limited to: carbonate, hydrochloride, hydrobromide, sulphate, hydrogen sulphate, citrate, maleate, fumarate, acetate, trifluoroacetate, 2-naphthalenesulphonate, and para-toluenesulphonate. Further information on pharmaceutically acceptable salts can be found in *Handbook of pharmaceutical salts*, P. Stahl, C. Wermuth, WILEY-VCH, 127-133, 2008, herein incorporated by reference.

The term "conventional SEC system" herein refers to a chromatographic system equipped with a concentration detector only. In some cases, the concentration detector may be a DRI or a UV detector. Thus, a conventional SEC system can be used to determine the absolute MWD of a sample if and only if it has been previously calibrated with suitable MW standards.

DESCRIPTION OF THE INVENTION

The present invention describes some analytical methods useful for assessing the molecular weight distribution (MWD) of glatiramoids. Glatiramoids are mixtures of amino acid copolymers containing L-glutamic acid, L-alanine, L-lysine and L-tyrosine residues in some specific proportions. In some cases such mixtures may have a composition similar to that of glatiramer acetate (GA), where the average molar ratio of the four amino acids is 0.141, 0.427, 0.338 and 0.095, respectively.

In a preferred embodiment the mixture to be analysed may have physicochemical and biological properties comparable to that of glatiramer acetate and may be intended for the preparation of a drug product therapeutically equivalent to Copaxone®. Thus, the method described herein can be used to distinguish glatiramer acetate from non-conforming copolymers.

In the method of the invention, glatiramoids and glatiramer acetate may be prepared following the manufacturing processes already described (Teitelbaum et al. 1971, U.S. Pat. No. 3,849,550, U.S. Pat. No. 5,800,808), herein incorporated by reference, which include the following steps:

Step (1): polymerisation of the protected amino acid precursors (N-carboxyanhydrides) to obtain a protected copolymer;

Step (2): deprotection of gamma-benzyl glutamate, using hydrobromic acid in acetic acid, and partial depolymerisation;

Step (3): deprotection of N-trifluoroacetyl lysine in aqueous piperidine;

Step (4): purification and freeze-drying.

The method described herein entails the use of conventional size exclusion chromatography (SEC) on a suitable chromatographic system, which is calibrated using a copolymer batch as a broad molecular weight standard. Broad standard calibration is a well-established method for the determination of the MWD of complex mixtures, such as low molecular weight heparins (2014). The method is also described in several course books and in pharmacopoeial monographs.

In the present invention, the broad standard should be a glatiramer-like polypeptide mixture and in some preferred cases it may be a mixture showing physicochemical and biological properties comparable to that of Copaxone®. In particular, the broad standard should be a mixture of polypeptides having the same higher order structure (and thus the same density or partial specific volume) as the polypeptides comprising Copaxone®.

In the method described herein, the MW of the broad standard can be determined by a number of complementary techniques such as osmometry, static light scattering, viscosimetry and analytical ultracentrifugation. In some cases the MWD of the broad standard can be characterised by a suitable mass spectrometry (MS) technique such as fast atom bombardment MS, matrix-assisted laser desorption ionization MS, or electrospray MS. In a preferred embodiment, the broad standard is fractionated by an optimised SEC system (column, elution buffer, flow, sample concentration, injection volume, etc) and analysed using a molar mass sensitive detector, such as MALS, coupled to a concentration detector, such as differential refractive index (DRI) detector or ultraviolet absorption (UV) detector, as for instance disclosed in as for instance disclosed in Olia et al., J. Pharm. Biomed. Anal. 25 (2001) 833-841, herein incorporated by reference.

The absolute MW of the copolymer can be determined at each volume increment using the Zimm plot approach. In this approach, the light scattering signal is assumed to be proportional to molar mass and sample concentration at any point of the chromatogram. Thus, a SEC system coupled to a MALS detector and a concentration detector (either DRI or UV) can accurately determine the overall molar mass distribution of the broad standard mixture. The cumulative MWD of the broad standard can be represented by tabulating the molecular weights corresponding to specified values of the cumulative area (expressed as a percent of the total peak area). This table should be intended as the certificate of analysis (CoA) of the broad standard and used for the calibration of a conventional SEC system.

Samples should be analysed on a conventional SEC system working under the same conditions (column, elution buffer, etc) used for the characterization of the broad standard. The broad standard and the samples should be analysed in the same analytical session or sequence. The chromatographic column should be calibrated by injecting the broad standard, recording the chromatogram, and determining the elution times corresponding to the cumulative weight fractions listed in the CoA. The calibration curve should be built by plotting the logarithm of the MWs listed in the CoA versus the corresponding elution times, and interpolating the points with a suitable decreasing function, such as a third-order polynomial or a linear function. In a preferred embodiment, the calibration curve can be a (decreasing) linear function.

For each sample, the MWD is determined by assigning, for each elution volume increment, the MW calculated through the calibration curve. The MWD may be represented by calculating the following parameters: peak average molecular weight ($M_p$), number average molecular weight ($M_n$), weight average molecular weight ($M_w$), Z average molecular weight ($M_z$) and molecular weight dispersity ($M_w/M_n$ and/or $M_z/M_w$). In addition, MWD can be represented by graphical tools (cumulative and differential MWD) and/or by tabulating the MW values for specified cumulative weight fractions. In some cases, the cumulative weight fractions may be the following: 10%, 50%, 90%. In other preferred cases, the cumulative weight fractions should be the following: 2.5%, 16%, 84%, 97.5%.

For each sample, lot or batch, the MWD parameters can be compared to a predetermined set of reference values, which are intended as release specifications for active pharmaceutical ingredients (APIs). The conformity to these specifications, alone or together with other quality criteria, may be used to decide whether or not the examined batch is suitable for therapeutic use. In a preferred embodiment, the batches showing a correct MWD profile, can be used for the manufacturing of injectable solutions containing 20 or 40 mg/ml of GA and 40 mg/ml of mannitol.

In some cases the method described herein can be used to analyse samples of injectable solution of Copaxone® RLD with the aim to establish the "sameness" criteria. For sameness assessment, proposed therapeutic equivalents (generic drugs) and commercial Copaxone® RLD samples should be analysed in the same analytical session and compared.

More in details, the present invention relates to a method for determining the molecular weight distribution of a ("sample") mixture of polypeptides (a), each of which polypeptide comprises L-glutamic acid, L-alanine, L-tyrosine and L-lysine, which method comprises subjecting said mixture of polypeptides (a) to chromatography, wherein the chromatographic column is calibrated by using a ("standard") mixture of polypeptides (b) having a known absolute molecular weight distribution, each of which polypeptide also comprises L-glutamic acid, L-alanine, L-tyrosine and L-lysine, to establish a relationship between retention time on the chromatographic column and the absolute molecular weight distribution.

According to an embodiment of the invention, the mixture of polypeptides (a) is a glatiramoid or a pharmaceutically acceptable salt thereof, preferably it is glatiramer acetate.

According to another embodiment, the absolute the molecular weight distribution of said mixture of polypeptides (b), comprises at least one molecular weight selected from: number average molar mass, weight average molar mass, Z average molar mass and cumulative molecular weight distribution; preferably, the absolute the molecular weight distribution of said mixture of polypeptides (b), comprises the number average molar mass, the weight average molar mass and the Z average molar mass.

According to another embodiment, determining the molecular weight distribution of said mixture of polypeptides (a), comprises determining at least one molecular weight selected from: number average molar mass, weight average molar mass, Z average molar mass and cumulative molecular weight distribution; preferably, it comprises determining the number average molar mass, the weight average molar mass and the Z average molar mass.

In an embodiment of the invention, the chromatography is size exclusion chromatography. More in details, the chromatographic column may be packed with a hydrophilic polymer gel or a hydrophilic-coated silica gel; preferably said hydrophilic-coated silica gel is a glyceropropyl-bonded silica gel. The cromatographic column is normally equipped with a concentration detector, preferably a UV detector.

In an embodiment of the invention, the absolute molecular weight distribution of the mixture of polypeptides (b) is determined by SEC-MALS, preferably by SEC-MALS-UV or SEC-MALS-RI, more preferably by SEC-MALS-UV.

Preferably, in the mixture of polypeptides (b), the molar fraction range of L-glutamic acid is 0.129-0.153, of L-alanine is 0.392-0.462, of L-tyrosine is 0.086-0.100, and of L-lysine is 0.300-0.374; more preferably, the molar fraction of L-glutamic acid is about 0.138, of L-alanine is about 0.434, of L-tyrosine is about 0.096, and of L-lysine is about 0.331.

According to another embodiment, the present invention also relates to a process for manufacturing a mixture of polypeptides (a), which comprises a method for determining the molecular weight distribution as disclosed above.

The following examples have the purpose of further illustrating the invention without however limiting it.

EXAMPLE 1

The polypeptide mixture was prepared by the method already described (Teitelbaum et al. 1971, U.S. Pat. No. 3,849,550, U.S. Pat. No. 5,800,808), herein incorporated by reference, which include the following steps:

Polymerisation of the Protected Amino Acid Precursors

The N-carboxyanhydrides of γ-benzyl-glutamate, alanine, tyrosine and ε-N-trifluoro-acetil-lysine (in average molar fractions of 0.141, 0.427, 0.095 and 0.338, respectively) are dissolved in anhydrous dioxane at room temperature and the polymerisation process is initiated by the addition of diethylamine. The reaction mixture is stirred at room temperature for 24 hours and then poured into purified water. The product is filtered, washed with water and dried to obtain a batch of protected copolymer.

Partial Depolymerisation and Deprotection of Gamma-Benzyl Glutamate

The protected copolymer mixture is treated with a solution of hydrobromic acid in acetic acid. The time needed to obtain a mixture of proper average molecular weight depends on the reaction temperature. A small scale test reaction is thus performed on every new batch: at different time periods (e.g. every hour) the average molecular weight is determined by SEC analysis, after removal of the remaining TFA group; a curve of molecular weight against the reaction time is drawn and the time needed for obtaining the target value is calculated and applied to the large scale reaction. The product obtained by the large scale reaction is finally poured into excess water, filtered, washed and dried, yielding the TFA-protected copolymer mixture.

Deprotection of N-Trifluoroacetyl Lysine in Aqueous Piperidine

TFA-protected copolymer is suspended in an aqueous solution of piperidine (1 mol/l) at a concentration of about 18 g/l. The mixture is stirred for 24 hours at room temperature and filtered. The solution of crude copolymer is ultra-filtered against water until a pH=8 is attained. Then acetic acid is added to the solution to have a pH in the range 4.0-4.5, and the copolymer is further ultrafiltered against water until its pH is in the range 5.5-6.0. This solution is then concentrated and freeze dried to obtain a batch of solid glatiramer acetate.

EXAMPLE 2

The broad standard was characterised by a variety of complementary techniques: nuclear magnetic resonance (NMR) spectroscopy, circular dichroism (CD) spectroscopy, size exclusion chromatography (SEC), amino acid analysis (AAA). Comparison of the results to those obtained from a batch of the reference listed drug (RLD) confirmed the similarity of the two copolymers.

NMR Spectroscopy

The polypeptide mixture (ca. 20 mg) was dissolved in deuterium oxide (0.75 ml). The $^1$H NMR spectrum was recorded on a Bruker Avance III spectrometer, operating at a proton frequency of 400 MHz and equipped with a 5-mm broadband inverse probe. The $^1$H spectrum exhibits a resonance pattern characteristic of the amino acid residues composing glatiramer acetate (see Table 1).

TABLE 1

| $^1$H chemical shifts (ppm) of the broad standard | |
|---|---|
| Chemical shift | Assignment |
| 1.34 | β-Ala, γ-Lys |
| 1.63 | δ-Lys |
| 1.76 | β-Lys |
| 1.85 | Acetate CH$_3$ |
| 2.00 | β-Glu |
| 2.22 | γ-Glu |

TABLE 1-continued

| $^1$H chemical shifts (ppm) of the broad standard | |
|---|---|
| Chemical shift | Assignment |
| 2.94 | ε-Lys, β-Tyr |
| 4.20 | α-(Ala, Lys, Glu) |
| 4.43 | α-Tyr |
| 6.76 | 3,5-Tyr |
| 7.06 | 2,6-Tyr |

The NMR spectrum of the broad standard was compared to that obtained from a sample of Copaxone® (batch #538823), which was previously dialysed against water in order to remove mannitol. Proton NMR spectra are reported in FIG. 1. The spectra show exactly the same profile (i.e. no additional or missing signals), confirming the similarity of the two samples.

CD Spectroscopy

CD is a spectroscopic method commonly used to study secondary structures (e.g., alpha helix and beta sheet) in proteins and polypeptides. The CD spectrum of glatiramer acetate represents a signature of the secondary structures of its polypeptides. The secondary structure is primarily determined by the amino acid sequence and length of a given polypeptide.

Figure 2:
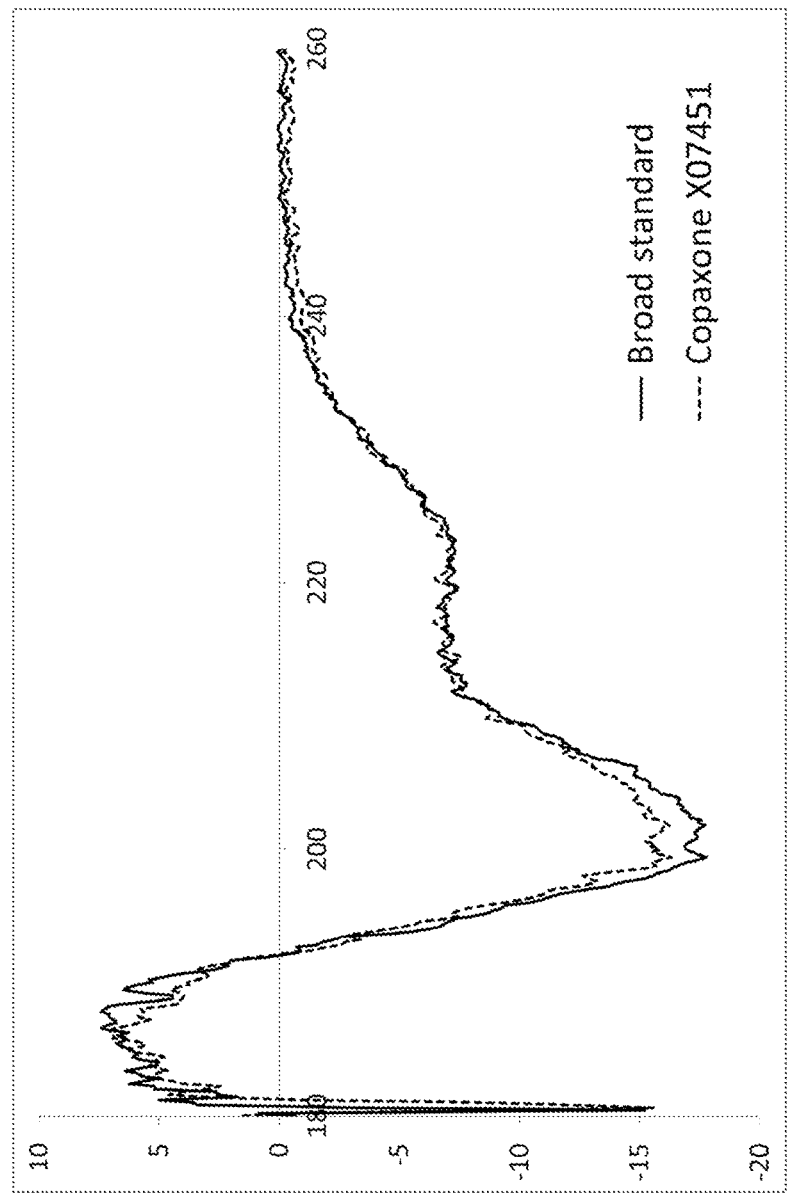
FIG. 2. CD spectra of the broad standard (solid line) and of a batch of Copaxone® (dashed line).

The broad standard and a batch of the RLD were separately dissolved in water (concentration: 0.1 mg/ml) and transferred to 0.1 cm path-length quartz cuvettes. The CD spectra were recorded in the 260-180 nm region. The spectra of the two samples are reported in FIG. 2. Comparison of the spectra suggests that the amino acid sequences and higher order structures of the two copolymers are comparable.

Size Exclusion Chromatography

Figure 3:
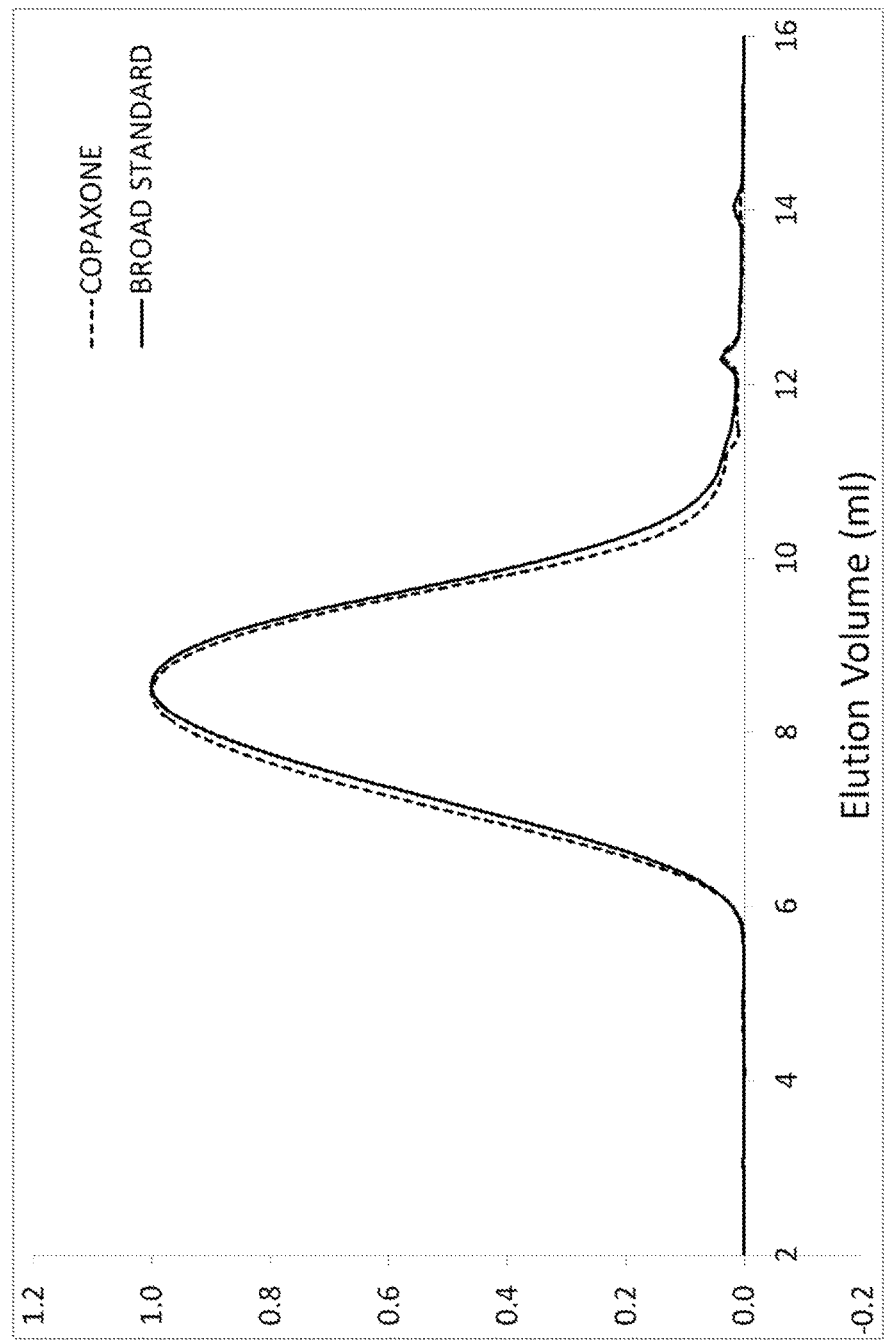
FIG. 3. SEC chromatograms of the broad standard (solid line) and of a batch of Copaxone® (dashed line).

The broad standard of the invention and a sample of Copaxone® (batch #X07341) were analysed by SEC (see Example 4). Comparison of the chromatograms (see FIG. 3) indicates that the MWD the two copolymers are comparable.

Amino Acid Analysis

The amino acid content of the broad standard was determined by a validated method which included quantitative hydrolysis of the sample and analysis by ion exchange chromatography with electrochemical detection. Results (expressed as molar fractions) were compared to the reference ranges.

TABLE 2

| Amino acid content of the broad standard | | |
|---|---|---|
| Amino acid | Molar Fraction | Molar Fraction Range |
| L-Glu | 0.138 | 0.129-0.153 |
| L-Ala | 0.434 | 0.392-0.462 |
| L-Tyr | 0.096 | 0.086-0.100 |
| L-Lys | 0.331 | 0.300-0.374 |

Results indicate that the composition of the broad standard falls within the specification limits reported for glatiramer acetate.

EXAMPLE 3

SEC-MALS-UV Analysis of the Broad Standard

The MWD of the broad standard was analysed by a modular multi-detector SEC system. The chromatographic system was an Alliance 2695 LC module from Waters (Milford, Mass., USA) equipped with two on-line detectors: a MALS Dawn DSP-F photometer from Wyatt Technology Corp. (Santa Barbara, Calif., USA), and a 996 Diode Array UV detector from Waters, used as the concentration detector. The MALS signal was recorded and elaborated through the software Astra 4.73.04, from Wyatt Technology Corp.

The UV spectrum of glatiramer acetate presents a shoulder at 220 nm, because of the absorption of peptide bonds (π-π* transition) and L-tyrosine aromatic side chains (π-π* transition). Accordingly, the mass concentration of the sample was assumed to be proportional to the UV signal at 220 nm.

Analyses were performed in the following chromatographic conditions:
  Column: BioSep SEC-s2000 (pore size: 145 Å; particle size: 5 μm; dimensions: 7.8×300 mm) from Phenomenex;
  Mobile phase: aqueous sodium phosphate 0.2 M, pH 3.0;
  Temperature: 35° C.;
  Degasser: vacuum;
  Flow rate: 0.5 mL/min;
  Injection Volume: 50 μL;
  Sample concentration: 3.0 mg/mL;
  Detection: UV at 220 nm;
  Data acquisition interval: 1 second. The Dawn DSP-F MALS photometer is an elastic or static or total intensity light scattering detector. The Dawn DSP-F MALS uses a vertically polarised He—Ne laser ($\lambda$=632.8 nm) and simultaneously measures the intensity of the scattered light at 15 fixed angular locations ranging, in aqueous buffers, from 14.5° to 158.3°. The MALS calibration constant was calculated using toluene as the standard, for which a Rayleigh factor R(q)=1.406 $10^{-5}$ $cm^{-1}$ was assumed. The normalization of the photodiodes was performed by measuring the scattering intensity of a narrow MW standard (pullulan, Mp=12.0 kg/mol, Mw/Mn<1.03, Rg=2.1 nm), which was considered an isotropic scatterer.

MALS data analysis requires a preliminary measurement of the specific refractive index increment (dn/dc) of the polymer with respect to the solvent. The dn/dc value was measured off-line by using a Chromatix KMX-16 differential refractometer. At 35° C., the dn/dc value of the samples (glatiramer acetate solution in mobile phase) was 0.186 mL/g.

Data Analysis and Characterization of the Broad Standard

The absolute molar mass of the copolymer was determined at each volume increment using the Zimm plot approach. In this approach, the light scattering signal is assumed to be proportional to molar mass and sample concentration (w/v) at any point of the chromatogram. Calculations were performed through the software Astra 4.73.04, from Wyatt Technology Corp.

Figure 4:
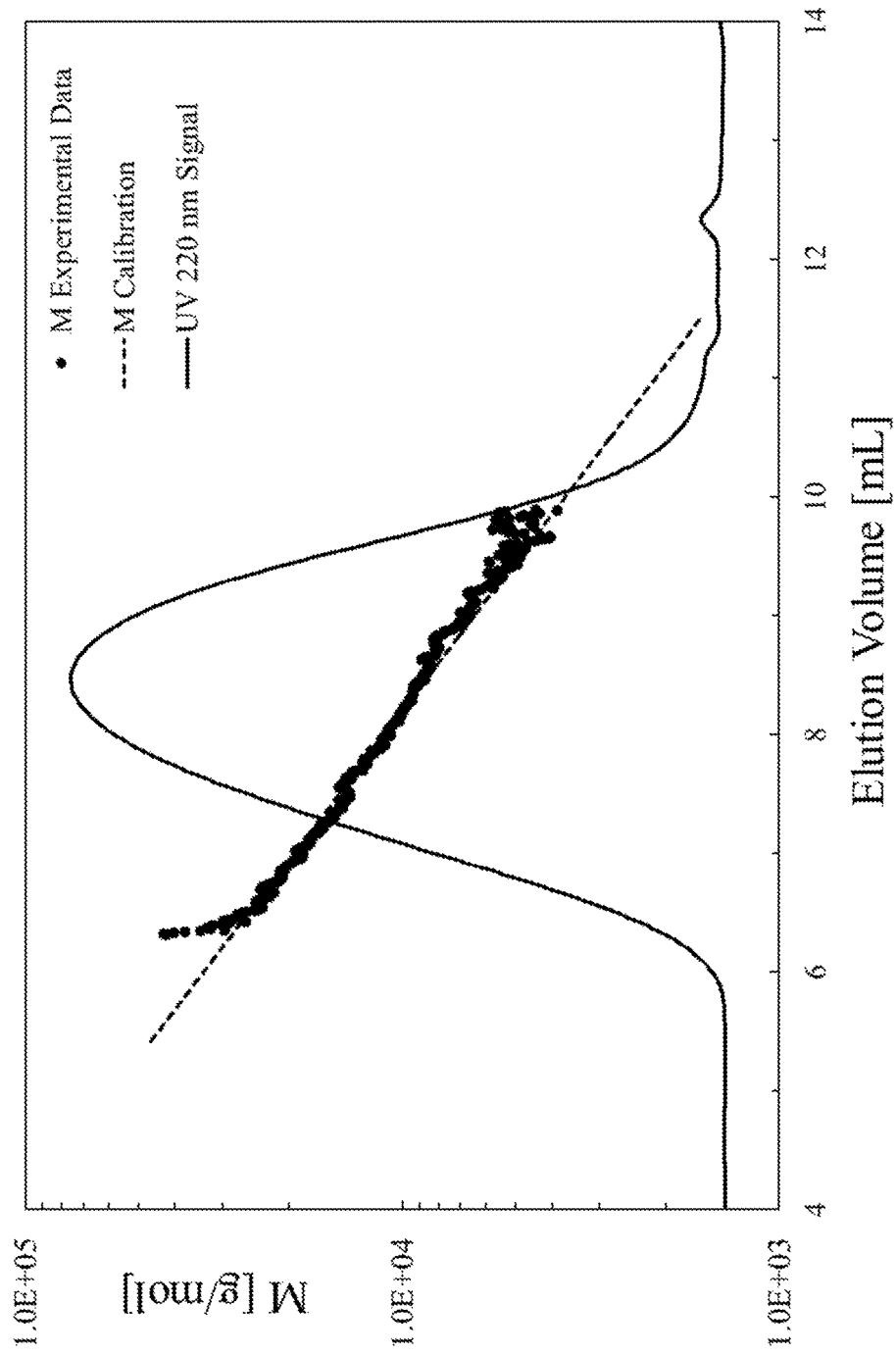
FIG. 4. Experimental and fitted calibration curve for the broad standard sample.

Because of the different sensitivity of the UV and MALS detectors, the signal-to-noise ratio at the extremities of the chromatogram (front and tail) is generally poor, and the accuracy of M results is not adequate (see FIG. 4). So, experimental data were divided in two regions: 1) a "Good Data Region", where the signal-to-noise ratio was excellent, which was substantially the central part of the chromatogram; 2) front and tail of the chromatogram. Experimental points of the good data region were fitted with a linear function:

$$\text{Log } M = A_0 + A_1 V$$

The good data region was selected by considering the highest number of experimental points that satisfied the followings conditions:

Coefficient of Determination: $R^2 > 0.99$;
Standard Error: SE<0.02.

Elution volumes between 6.267 mL and 9.433 mL were selected (a large data interval containing 381 experimental points).

The resulting calibration curve (see FIG. 4) is characterised by following parameters:
  Intercept: $A_0$=5.9239;
  Slope: $A_1$=−0.2386;
  Coefficient of Determination: $R^2$=0.9933;
  Standard Error: SE=0.0181.

Figure 5:
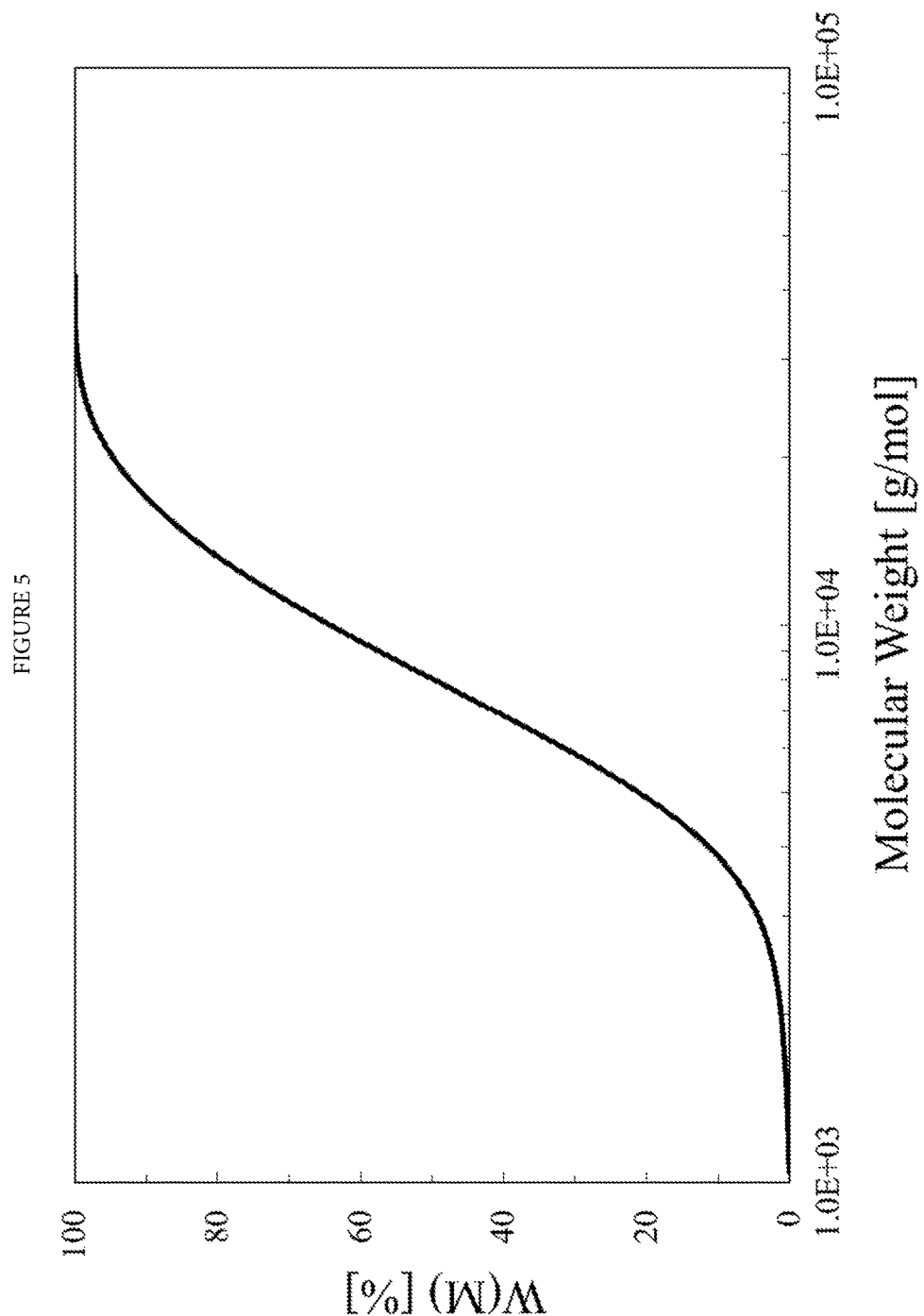
FIG. 5. Cumulative molar mass distribution of the broad standard. It describes the growth of the weight fraction (%) as function of Log M.
Figure 6:
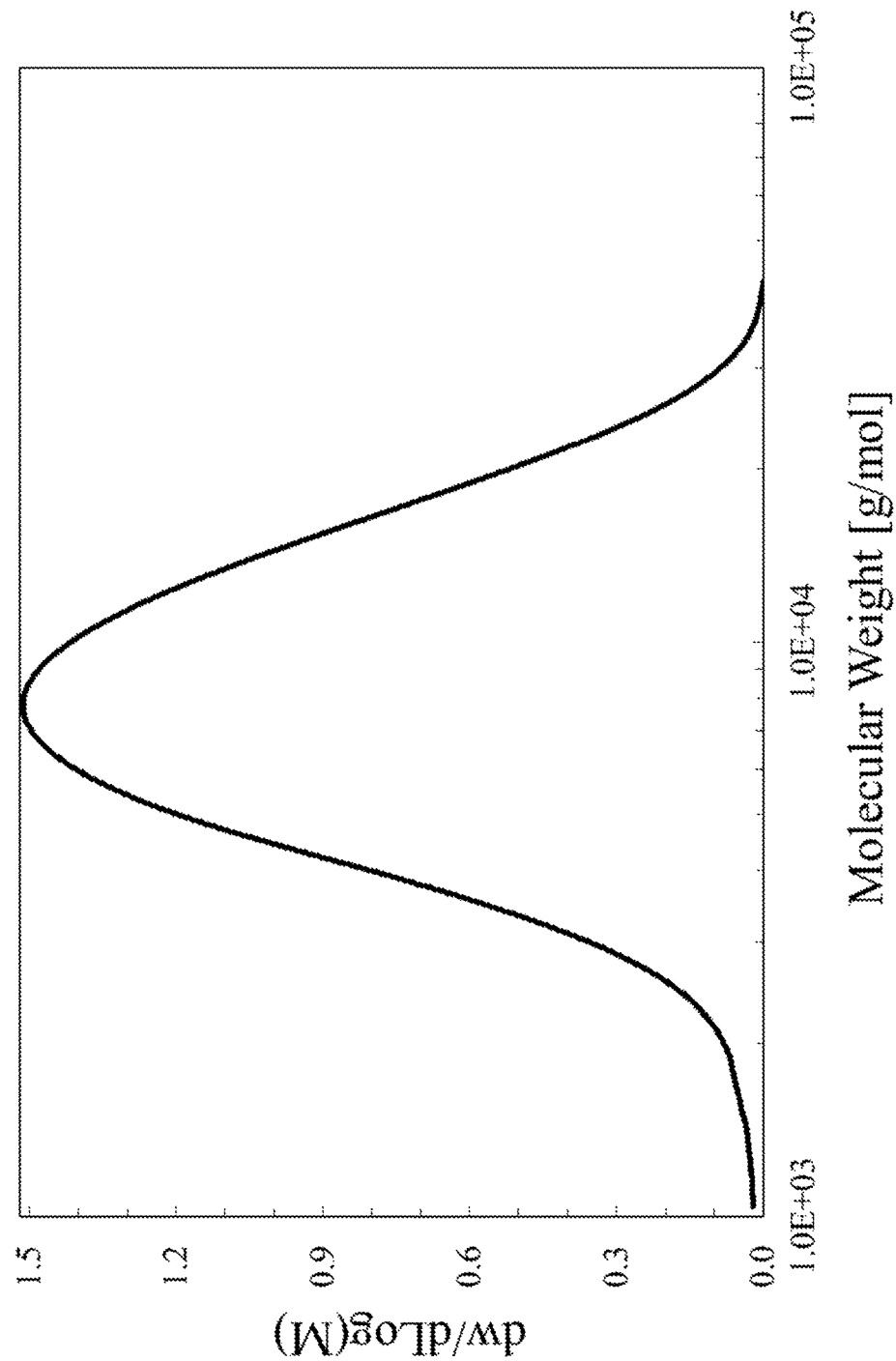
FIG. 6. Differential molar mass distribution of the broad standard.

The calibration curve was used to determine the cumulative and differential MWD of the broad standard (see FIGS. 5 and 6). The cumulative MWD was also tabulated by reporting the MW values for specified cumulative weight fractions (see Table 3). This table was considered as the certificate of analysis of the broad standard and used for the calibration of a conventional SEC system (see Example 4).

TABLE 3

Broad standard table (cumulative MWD)

| Percent area | Molar mass |
|---|---|
| 1 | 25000 |
| 5 | 18800 |
| 10 | 15800 |
| 20 | 12500 |
| 30 | 10500 |
| 40 | 8950 |
| 50 | 7760 |
| 60 | 6690 |
| 70 | 5750 |
| 80 | 4860 |
| 90 | 3860 |
| 95 | 3170 |
| 99 | 1990 |

From the whole MWD the molar mass moments ($M_n$, $M_w$, $M_z$) and dispersity (D=$M_w/M_n$) were calculated. Results are reported in Table 4.

TABLE 4

Molar mass moments and dispersity of the broad standard

| $M_n$ (Da) | $M_w$ (Da) | $M_z$ (Da) | Dispersity |
|---|---|---|---|
| 6600 | 8920 | 11680 | 1.35 |

Comparison of the Broad Standard to the Reference Listed Drug

Figure 7:
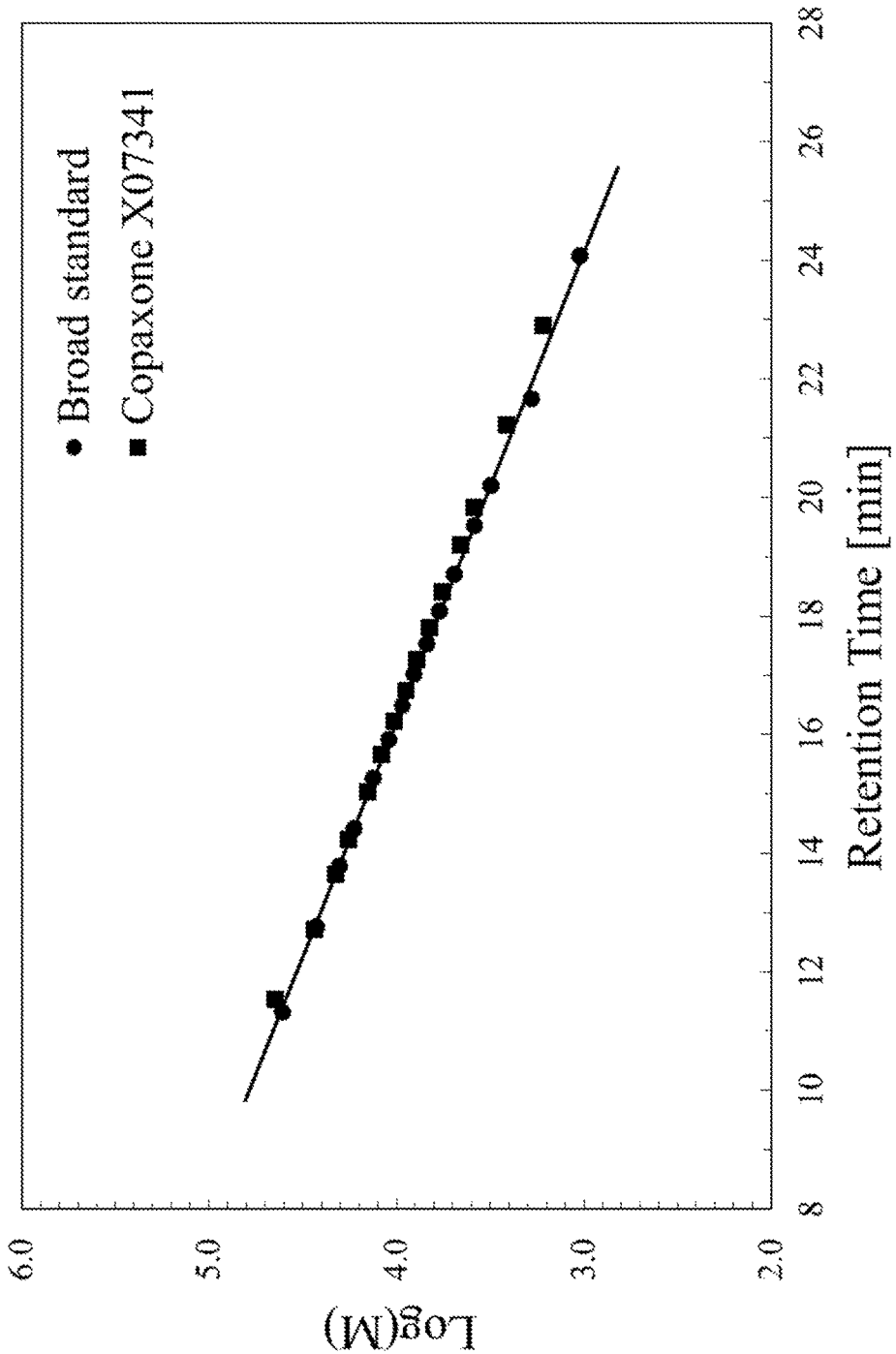
FIG. 7. Comparison of the calibration curves (log M vs. $T_R$) obtained from: a batch of the broad standard of the invention (circles); a batch of Copaxone® (#X07341, squares).

A batch of Copaxone® was characterised by the method described above and compared to the broad standard of the invention. Comparison of the two calibration curves (see FIG. 7) indicates that the relationship between elution volume (or retention time) and molecular weight found for the broad standard is comparable to that found for Copaxone®. This is consistent with CD results (see Example 2), which showed similarity of the higher order structures of the two copolymers.

EXAMPLE 4

Analysis of Glatiramer Acetate Samples

Samples and the broad standard (solids or injectable solutions) were diluted to 3.0 mg/ml with the elution buffer and analysed on a Prominence LC-20AB liquid chromatography system equipped with a SPD-20A UV-visible detector (both from Shimadzu Corporation). Analyses were performed in the same chromatographic conditions described in Example 3. Chromatogram acquisition and data analysis were performed through the software Clarity Chromatography Station—GPC Extension (from DataApex).

For the broad standard chromatogram, the software calculates the total area under the glatiramer peak and the cumulative area at each point as a percent of the total. Then it identifies the points in the chromatogram which correspond to the percent fractions listed in the broad standard table, and assigns the MWs listed in the table to the corresponding retention times ($T_R$). The calibration curve is then built by fitting log MW vs. $T_R$ to a linear function.

For each sample chromatogram, the software calculates the total area under the glatiramer peak and the cumulative area at each point as a percent of the total. By applying the calibration curve, the software assigns the corresponding MW ($M_i$) to each point under the glatiramer peak, and calculates the following parameters:

Peak average molecular weight, $M_p$;

Number average molecular weight, $M_n = \Sigma(N_i M_i)/\Sigma M_i = \Sigma H_i / \Sigma(H_i/M_i)$;

Weight average molecular weight, $M_w = \Sigma(N_i M_i^2)/\Sigma(N_i M_i) = \Sigma(H_i M_i)/\Sigma H_i$;

where $N_i$ is the number of molecules with molar mass $M_i$ and $H_i$ is the detector response at the ith point of the chromatogram;

Dispersity, $D = M_w/M_n$;

The molecular weights corresponding to the following values of the cumulative area: 2.5, 16.0, 84.0, 97.5 percent ($M_{2.5}$, $M_{16}$, $M_{84}$, $M_{97.5}$).

The calibration curve was used for calculating the MWD parameters of six RLD batches (see Table 5). These parameters were then employed for assessing the acceptance criteria for choosing glatiramer acetate batches suitable for pharmaceutical use.

TABLE 5

MWD parameters of six Copaxone ® RLD batches

| Batch | $M_p$ | $M_n$ | $M_w$ | D | $M_{2.5}$ | $M_{16}$ | $M_{84}$ | $M_{97.5}$ |
|---|---|---|---|---|---|---|---|---|
| X06251 | 7038 | 6643 | 8758 | 1.32 | 20841 | 12802 | 4350 | 2736 |
| X06611 | 7972 | 7230 | 9594 | 1.33 | 22521 | 14143 | 4696 | 2920 |
| X06771 | 7263 | 7030 | 8996 | 1.28 | 20653 | 13001 | 4689 | 3048 |
| X07181 | 7446 | 6856 | 8977 | 1.31 | 20617 | 13137 | 4540 | 2838 |
| P63037 | 7450 | 6928 | 9251 | 1.34 | 22224 | 13628 | 4497 | 2788 |
| X07341 | 8131 | 7152 | 9526 | 1.33 | 21942 | 14079 | 4674 | 2838 |

The invention claimed is:

1. A method for determining the molecular weight distribution of glatiramer acetate, which method comprises subjecting said glatiramer acetate to size exclusion chromatography, wherein the chromatographic column is calibrated by injecting a broad molecular weight standard which consists of a mixture of polypeptides having a known absolute molecular weight distribution, each of which polypeptide comprises L-glutamic acid, L-alanine, L-tyrosine and L-lysine.

2. The method according to claim 1, wherein the absolute molecular weight distribution of said broad molecular weight standard comprises at least one molecular weight selected from: number average molar mass, weight average molar mass, Z-average molar mass and cumulative molecular weight distribution.

3. The method according to claim 1, wherein the absolute molecular weight distribution of said broad molecular weight standard comprises the number average molar mass, the weight average molar mass and the Z-average molar mass.

4. The method according to claim 1, wherein determining the molecular weight distribution of glatiramer acetate said comprises determining at least one molecular weight selected from: number average molar mass, weight average molar mass, Z-average molar mass and cumulative molecular weight distribution.

5. The method according to claim 1, wherein determining the molecular weight distribution of said glatiramer acetate, comprises determining the number average molar mass, the weight average molar mass and the Z-average molar mass.

6. The method according to claim 1, wherein said chromatographic column is packed with a hydrophilic polymer gel or a hydrophilic-coated silica gel, preferably said hydrophilic-coated silica gel is a glyceropropyl-bonded silica gel.

7. The method according to claim 1, wherein said chromatographic column is equipped with a concentration detector, preferably a UV detector.

8. The method according to claim 1, wherein the absolute molecular weight distribution of the broad molecular weight standard is determined by SEC-MALS.

9. The method according to claim 1, wherein the absolute molecular weight distribution of the broad molecular weight standard is determined by SEC-MALS-UV or SEC-MALS-RI, preferably by SEC-MALS-UV.

10. The method of claim 1, wherein, in the broad molecular weight standard, the molar fraction range of L-glutamic acid is 0.129-0.153, of L-alanine is 0.392-0.462, of L-tyrosine is 0.086-0.100, and of L-lysine is 0.300-0.374.

11. The method of claim 1, wherein, in the broad molecular weight standard, the molar fraction of L-glutamic acid is about 0.138, of L-alanine is about 0.434, of L-tyrosine is about 0.096, and of L-lysine is about 0.331.

12. The method of claim 1, wherein the broad molecular weight standard has a dispersity of about 1.35.

13. The method of claim 1, wherein the broad molecular weight standard has a Mn of about 6600 Da.

14. The method of claim 1, wherein the broad molecular weight standard has a Mw of about 8920 Da.

15. The method of claim 1, wherein the broad molecular weight standard has a Mz of about 11680 Da.

16. A process for manufacturing glatiramer acetate, which comprises a method for determining the molecular weight distribution according to claim 1.

* * * * *